United States Patent [19]

Adet et al.

[11] Patent Number: 4,689,301
[45] Date of Patent: Aug. 25, 1987

[54] TRANSPARENT POLYURETHANE FOAM WALL

[75] Inventors: Bruno Adet, Marseilles; Claude Gudin, Aix; Catherine Thepenier, Pertuis, all of France

[73] Assignee: Commissariat a l'Energie Atomique, Paris, France

[21] Appl. No.: 622,168

[22] Filed: Jun. 19, 1984

[30] Foreign Application Priority Data

Jun. 24, 1983 [FR] France .................... 83 10489

[51] Int. Cl.$^4$ ............................................. C12M 3/00
[52] U.S. Cl. ............................. 435/284; 435/288; 435/813; 47/1.4; 47/58
[58] Field of Search ............... 435/246, 285, 287, 288, 435/813, 299; 47/1.4, 58

[56] References Cited

U.S. PATENT DOCUMENTS

| | | | |
|---|---|---|---|
| 2,732,663 | 1/1956 | Dewey, II | 47/1.4 |
| 3,941,662 | 3/1976 | Munder et al. | 435/284 |
| 3,948,732 | 4/1976 | Haddad et al. | 435/285 |
| 3,949,742 | 4/1976 | Nowakowski | 128/155 |
| 3,955,317 | 5/1976 | Gudin | 435/288 |
| 4,225,671 | 9/1980 | Puchinger et al. | 435/285 X |
| 4,250,267 | 2/1981 | Hartdegen et al. | 435/317 |
| 4,442,206 | 4/1984 | Michaels et al. | 435/284 X |
| 4,446,236 | 5/1984 | Clyde | 435/287 |
| 4,463,522 | 8/1984 | Lindemann | 435/284 X |
| 4,565,783 | 1/1986 | Hansen et al. | 435/299 |

FOREIGN PATENT DOCUMENTS 2084155  4/1982  United Kingdom .

OTHER PUBLICATIONS

Sol. Energy R. & D Eur. Community, vol. 1, Sec. D, 1982, pp. 134–139 (BE); M. Brouers et al: "Immobilization and Stabilization of Green and Blue Green Algae in Crosslinked Serumalbumin Glutaraldehyde and in Polyurethane Matrices". *p. 134, resume; p. 136, point 2.2–p. 137, point 2.2.3*.

Primary Examiner—Alan Cohan
Assistant Examiner—John A. Rivell

[57] ABSTRACT

The invention relates to a transparent polyurethane foam wall optionally containing microorganisms, and a process for the preparation thereof, and the use of this wall in a biophotoreactor. This wall has pores, in which are distributed microorganisms and the pores are closed on one of the faces of the wall, in such a way that said face is impermeable to liquids and gases, while the other face of the wall has an open porosity. Thus, by circulating a liquid nutrient medium and a gas along the second face of the wall and exposing the first face thereof to light, it is possible to culture microorganisms and collect the metabolites formed by them in the liquid medium.

15 Claims, 4 Drawing Figures

TRANSPARENT POLYURETHANE FOAM WALL

BACKGROUND OF THE INVENTION

The present invention relates to a transparent polyurethane foam wall containing microorganisms, and a process for the preparation thereof and its use in a biophotoreactor.

Over the past few years, new procedures have been developed for culturing microorganisms able to grow under the action of light, in the presence of carbon dioxide gas and an appropriate culture medium, for forming products having an economic interest in connection with foods, pharmacy and the assisted recovery of petroleum.

Thus, certain microorganisms, e.g. the microrhodophyceae *Porphyridium cruentum*, is able to excrete sulphated polysaccharides having a significant economic value. By culturing microorganisms such as *Botryococcus braunii*, it is possible to obtain hydrocarbons which are also of significant interest.

In order to obtain such microorganism cultures, it is necessary to bring them into contact with an appropriate nutrient liquid medium and with carbon dioxide gas and to simultaneously expose the microorganisms to sunlight or artificial light. The product synthesized by the microorganism can then be extracted from the nutrient liquid medium. These cultures are generally produced in biophotoreactors designed so as to ensure an irradiation of the microorganisms by sunlight or artificial light, and a contacting thereof with an appropriate medium.

For example, a biophotoreactor of this type is described in U.S. Pat. No. 3,955,317 published on May 11th 1976. According to this patent, the biophotoreactor is constituted by a tubular system which is transparent to solar radiation, which contains microalgae suspended in a nutrient liquid into which is injected carbon dioxide gas. The vegetable cells bring about the photopolymerization of the carbon dioxide gas into a desired chemical product, e.g. a product having a food or pharmaceutical use, or into a hydrocarbon, as a function of the microalgae used, and said reaction is also accompanied by a release of oxygen. To prevent premature sedimentation of the celluar biomass within the reactor, it is necessary to keep the latter in motion. This can be brought about by using a tubular system which is open at both ends and by continuously injecting into the intake a mixture of nutrient liquid and microalgae, the mixture being extracted from the outlet. The microalgae and the metabolites produced by the latter are then separated from the liquid medium by centrifuging.

The use of a biophotoreactor of this type suffers from certain disadvantages because it requires a large amount of energy on the one hand for circulating the microalgae, and on the other for separating the metabolites, which increases the cost of the thus produced products.

In order to reduce the energy used, consideration has been given to the immobilization of the microalgae in a spongy polyurethane foam structure, such as that described in the report of the Academie des Sciences of 6.7.1981, vol. 293, series III, pp. 35-37 and entitled "Production of sulphated polysaccharides by a biophotoreactor having immobilized *Porphyridium cruentum* cells". In this case, the microorganisms are introduced at the time of preparing the polyurethane foam by mixing in substantially equal parts the polyurethane foam precursor compositions and a suspension of algae in a nutrient liquid. The formation of the foam and the immobilization of the microalgae within the latter take place simultaneously within a few dozen minutes at ambient temperature. The foam is then cut into small dices of approximate side length 1.5 cm. They are then introduced into a glass column containing a liquid nutrient medium and are exposed to sunlight.

The microalgae which survive the polymerization then recolonize all the pores of the polyurethane dices, which are continuously irrigated by the liquid nutrient medium and by the air containing 2% carbon dioxide gas. As in the previous case, the microalgae absorb solar radiation and the carbon from the carbon dioxide gas and produce hydrosoluble polysaccharides which they reject through the pores into the liquid nutrient medium. Although this type of reactor makes it possible to considerably reduce energy costs, it still suffers from certain disadvantages.

Thus, the polyurethane dices are not very transparent and therefore the solar radiation only weakly reaches those dices located in the centre of the tube. Moreover, difficulties are encountered in transferring the materials (carbon dioxide gas supply and polysaccharide extraction).

SUMMARY OF THE INVENTION

The problem of the invention is to provide a transparent polyurethane foam wall containing the microorganisms and which can be used in a biophotoreactor to obviate the aforementioned disadvantages.

The invention also relates to a transparent polyurethane foam wall which is characterized in that it has an open porosity on at least one of its faces.

According to a preferred embodiment of the invention, the transparent wall also contains microorganisms so as to be usable in a biophotoreactor. In this case, the transparent wall is constituted by polyurethane foams in the pores of which are distributed the microorganisms and it is characterized in that the foam pores are closed on one of the faces of the wall so that said face is impermeable to the liquids and gases, whilst the opposite face of the wall has an open porosity.

Due to the different permeability characteristics of the two opposite faces of the wall, the latter makes it possible to ensure culturing of the microorganisms under good conditions. Thus, the impermeable face of the wall can be exposed to radiation, whilst the opposite face having an open porosity can be in contact with a liquid nutrient medium, which can have easy access to the interior of the wall in order to supply the necessary constituents for their development to the microorganisms immobilized in said wall. In the same way, the products synthesized by the microorganisms can be discharged into the liquid nutrient medium in contact with the face of the wall having an open porosity.

Thus, it is not only possible to limit the energy costs as in the case of using polyurethane dices on which the microorganisms are immobilized, but it is also possible to bring about irradiation by solar radiation and material transfers under much better conditions.

The microorganisms distributed in the pores of the wall can be constituted by microalgae such as *Porphyridium cruentum* and *Botryococcus braunii*, or by bacteria, such as photosynthetic bacteria.

The invention also relates to a process for the preparation of a transparent polyurethane foam wall, whereof at least one of the faces has an open porosity. This process comprises the following stages:
  (a) preparing a liquid mixture incorporating the precursor compositions of the polyurethane foam,
  (b) introducing this mixture into a mould having several walls, whereof at least one has been impregnated with an agent able to open the pores of the foam,
  (c) forming the polyurethane foam by reacting the precursor compositions, and
  (d) removing from the mould the thus obtained wall.

When it is wished to simultaneously introduce the microorganisms into the wall, the process comprises the following stages:
  (a) preparing a liquid mixture comprising polyurethane foam precursor compositions and a suspension of microorganisms in a liquid nutrient medium,
  (b) introducing the mixture into a mould having two opposite walls, whereof only one has been impregnated with an agent able to open the pores of the foam,
  (c) forming the plastic material foam by reacting the precursor compositions present in the liquid mixture, and
  (d) removing the thus obtained wall from the mould.

Due to the presence of an agent able to open the pores of the foam on one of the walls of the mould, following mould removal a wall is obtained which is porous on its face which was in contact with the wall of the mould impregnated with the agent able to open the pores of the foam, whilst being impermeable to gases and liquids on its other face which was in contact with the other wall of the mould. Thus, the agent able to open the pores is diluted on the foam surface during formation, and embrittles the walls of the pores. Thus, during the expansion of the foam, the embrittled walls tear and consequently the pores open towards the outside. However, on the other wall of the mould which was not impregnated with this agent, a continuous, transparent skin is obtained, which is impermeable as a result of the concentration of material during the expansion of the foam.

According to the invention, the agent able to open the pores of the foam can be a polyoxyalkylene with a high ethylene oxide content, e.g. polyethylene glycol, such as PEG400, can also be a polyester polyol or an alkanol amine.

The precursor compositions of the polyurethane foams are compositions able to react with one another to form said foam. They are generally constituted by a polyether polyol based on propylene oxide and ethylene oxide and by toluene diisocyanate.

In exemplified manner, these compositions can be constituted by urethane prepolymers, marketed by TOYO RUBER AND Co, which are respectively constituted by a polyether diol having an average molecular weight of approximately 2600 and containing 91% ethylene oxide, and by a polyether diol having an average molecular weight of approximately 2600 and an ethylene oxide content of 100%, the NCO content of the two prepolymers being 4%. It is also possible to use prepolymers marketed under the trademark HYPOL 3000 by Messrs. W. R. Grace and which also contain approximately 10% by weight of free toluene diisocyanate, or prepolymers marketed by Montedison having a 5% free NCO content and which require the use of specific alkaline catalysts for foam formation.

In order to form the liquid mixture used for the preparation of the wall, in general one part of the liquid precursor prepolymer of the polyurethane foam which can contain up to 50% water is mixed with one part of a suspension of microorganisms in a liquid nutrient medium.

Generally the microorganisms concentration of the suspension is 2 to 20 mg of dry matter per liter and the liquid nutrient media used are conventionally constituted by the media conventionally employed for growing microorganisms. These media contain numerous constituents, e.g. compounds of nitrogen, phosphorus, potassium, calcium and/or magnesium, salts of iron, zinc, manganese, copper, nickel, molybdenum and/or boron. They can also contain growth regulators and optionally aminoacids and vitamins and their contents of these various constituents are chosen as a function of the nature of the microorganism used.

According to the invention, the opposite walls of the mould can be constituted either by concentric tubes, or by flat plates. Thus, it is possible to obtain the transparent wall according to the invention either in the form of a tube, whose face having an open porosity generally constitutes the inner surface of the tube, or in the form of a plate, whereof one of the faces is impermeable to the liquids and gases, whilst the other face is permeable to the liquids and gases.

In general, the gap between the two walls of the mould which will determine the thickness of the transparent wall prepared according to the invention is 1 to 5 mm and the mould walls are made from a metallic material, e.g. steel.

Before introducing the liquid mixture into the mould, the mould wall is impregnated with alkylene polyoxide, e.g. by brush application, which is followed by the introduction of a liquid mixture and the closure of the mould. After this operation, the foam forms in the mould at ambient temperature and the polymerization and hardening of the foam are ended after approximately one hour. The thus obtained transparent wall is then removed from the mould.

The invention also relates to a biophotoreactor for culturing microorganisms and which comprises at least one transparent wall containing the microorganisms and having the permeability characteristics given hereinbefore, the face of said wall which is impermeable to the gases and liquids being exposed to a light source, and the opposite face of said wall having an open porosity is in contact with a liquid nutrient medium and with a gas for bringing about the growth of the microorganisms present in said wall and for permitting them to synthesize the desired products.

According to a first embodiment of this biophotoreactor, the latter only has a single transparent wall and it is used for culturing only one type of microorganism. In this case, the transparent wall is advantageously shaped like a tube, whereof the outer surface constitutes the face impermeable to the gases and the liquids and the nutrient medium and a gas are circulated within said tube to bring about the growth of the microorganisms present in the wall.

According to a second embodiment of the biophotoreactor according to the invention, and which is particularly suitable for the growth of two types of microorganisms, the latter comprises two superimposed transparent walls defining between them gap for the circulation of the first liquid nutrient medium and a first gas and in this case the face which is impermeable to the gases and the liquids of the second transparent wall positioned beneath the first transparent wall is in contact with the first liquid nutrient medium circulating in the gap between the two walls, whilst the face having an open porisity of the second transparent wall is in contact with the second liquid nutrient medium and the second gas for ensuring the growth of the microorganisms in the second wall.

This embodiment of the biophotoreactor according to the invention is particularly suitable for the growth on the one hand of micro-algae using one part of the light spectrum and located in the first wall, and on the other hand photosynthetic bacteria using the complementary part of the light spectrum and located in the second wall.

According to a third embodiment of the biophotoreactor according to the invention, the latter comprises two superimposed transparent walls defining between them a gap in which is circulated a liquid nutrient medium, the face having the open porisity of the first transparent wall and which is located above the second transparent wall in contact with the liquid nutrient medium and the face having the open porosity of the second transparent wall is also in contact with the liquid nutrient medium.

This arrangement with two walls is particularly suitable for culturing microorganisms able to release oxygen and which are distributed in the pores of the first transparent wall, thereby releasing the oxygen into the liquid nutrient medium. In this case, the microorganisms present in the second transparent wall are microorganisms using oxygen for their growth and they can consequently consume the oxygen released into the nutrient medium by the microorganisms present in the first wall.

BRIEF DESCRIPTION OF THE DRAWINGS

The invention is described in greater detail hereinafter relative to non-limitative embodiments and the attached drawings, wherein show.

DETAILED DESCRIPTION OF THE PREFERRED EMBODIMENTS

Figure 1:
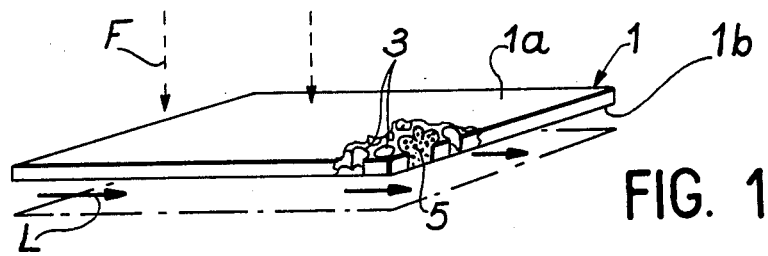
FIGS. 1 and 2 two embodiments of the transparent wall according to the invention.

FIG. 1 shows a first embodiment of the transparent wall according to the invention and its use in a biophotoreactor only having a single transparent wall.

Figure 2:
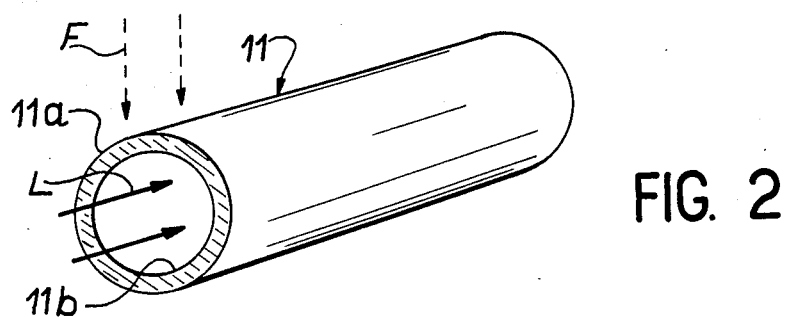

In FIG. 1, 1 designates the transparent wall according to the invention which is formed from polyurethane foam in whose pores 3 are distributed microorganisms 5. The transparent wall is in the form of a flat plate and its upper face $1a$ is impermeable to gases and liquids, whereas its lower face $1b$ is permeable to the gases and liquids. The inner face $1b$ is in contact with a liquid flow L, which flows along the wall in order to on one hand supply the elements necessary for culturing the microorganisms and on the other hand to extract the metabolites formed by said microorganism. The upper face $1a$ of the wall is exposed to radiation, symbolized by arrows F, which can be emitted by the sun or by an artificial light source. FIG. 2 shows another embodiment of the transparent wall according to the invention. As hereinbefore, the wall 11 is made from polyurethane foam, in whose pores are distributed microorganisms and which is shaped like a tube. The outer surface of tube $11a$ is impermeable to gases and liquids, whereas the inner surface $11b$ is permeable to the gases and liquids. Thus, it is possible to expose the outer surface $11a$ to radiation F and circulate within said tube liquid medium L able on the one hand to supply the elements necessary for the growth of the microorganisms and able on the other hand to extract the products synthesized by the same.

Figure 3:
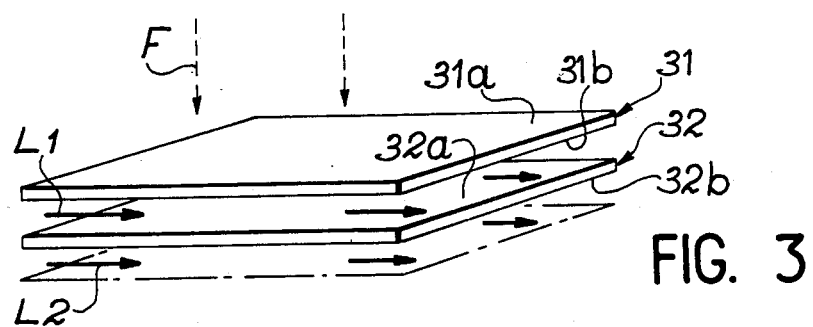
FIG. 3 diagrammatically the arrangement of the two transparent walls in a biophotoreactor.

FIG. 3 shows an embodiment of the biophotoreactor according to the invention in which it has two superimposed transparent walls. References 31 and 32 designate two flat walls, between which is circulated a first nutrient medium $L_1$. The first wall 31 is located in the upper part of the device with its face which is permeable to the gases and liquids $31b$ in contact with the first liquid medium $L_1$. The second transparent wall 32 is positioned beneath the first wall 31, so that its face $32a$ which is impermeable to gases and liquids is in contact with the first liquid medium $L_1$. Below the second transparent wall 32 is circulated a second liquid nutrient medium $L_2$. Thus, by exposing the assembly to a light source, symbolized by arrows F, it is possible to ensure the growth of the microorganisms located in the first transparent wall 31 and to collect in the first liquid $L_1$ the metabolites formed by these microorganisms and to bring about the growth of second microorganisms in the second transparent wall 32 by supplying thereto the elements necessary for their growth and extract the metabolites formed by the second microorganisms from said second liquid medium $L_2$. In this case, the first microorganisms use a first part of the light spectrum and the second microorganisms use the complementary part of said light spectrum for their growth.

For example, the first microorganisms can be constituted by microalgae, such as *Porphyridium cruentum* or *Botryococcus braunii* and the second microorganisms can be constituted by photosynthetic bacteria.

Figure 4:
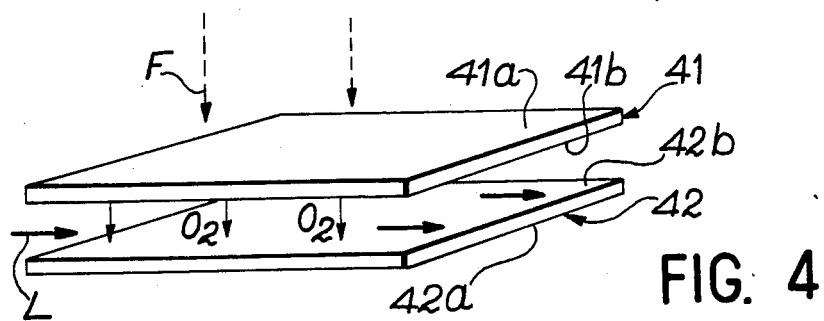
FIG. 4 another arrangement of the two transparent walls in a biophotoreactor.

FIG. 4 shows another embodiment of a biophotoreactor having two transparent walls according to the invention. It is possible to see that the biophotoreactor comprises a first transparent wall 41 and a second transparent wall 42. The first wall 41 is arranged in such a way that its face $41b$ which is permeable to the gases and liquids, is in contact with a liquid nutrient medium L circulating between the two walls, whilst the second wall 42 is positioned below the first wall 41 in such a way that its face $42b$, which is permeable to the gases and liquids, is also in contact with the liquid nutrient medium L. Thus, by irradiating the upper part $41a$ of the photoreactor by means of a light source, the microorganisms present in the first transparent wall 41 are grown. These microorganisms release into the liquid nutrient medium L elements which can be used for the growth of the microorganisms present in the second transparent wall 42 and the products synthesized by the first and/or second microorganisms are extracted from the liquid nutrient medium.

For example, the first wall 41 can incorporate microalgae able to release oxygen into the liquid medium and said oxygen can be used by microorganisms present in the second transparent wall 42.

The following example of a transparent wall illustrates the invention. The polyurethane foam precursor composition used in this case is a polyether polyol prepolymer based on propylene oxide (80%) and ethylene oxide (20%), as well as toluene diisocyanate, in such a way that there is a 1.45 excess of groups —N=C=O and a —NCO:OH ratio of 1.87. To the prepolymer are added 50% of a suspension of Porphyridium cruentum microorganisms obtained by dilution in 500 ml of Hemerick medium, of 37 g of a 90% water-containing microorganism paste obtained by culturing under the following conditions: 25%, liquid mineral Hemerick medium at pH 6.9, bubbling with 5% $CO_2$-containing air at a rate of 10 volumes/volume of culture and per hour.

This mixture is introduced into a flat steel mould, whose bottom has been impregnated with polyethylene glycol, PEG 400 of molecular weight 400 by brush application.

After approximately 1 hour at ambiant temperature, the wall obtained is removed from the mould. The face of this wall was in contact with the PEG 400 has an open porosity, whilst the other faces of the wall are impermeable to the gases and liquids.

This wall is used as the upper wall of a biophotoreactor and its impermeable face is exposed to a light source, such that the energy received thereon is 28 $Wm^{-2}$ or 578 $kcal.m^{-2}day^{-1}$ and on the other face is circulated the mineral Hemerick medium at pH 6.9 and air containing 2% $CO_2$. The sulphated polysaccharides formed by the Ramus method are extracted from the medium leaving the biophotoreactor.

What is claimed is:

1. A transparent wall made from polyurethane foam, in whose pores are distributed microorganisms, wherein the pores of the foam are closed on one of the faces of the wall in such a way that said face is impermeable to liquids and gases, whilst the opposite face of the wall has an open porosity.

2. A wall according to claim 1, wherein the microorganisms are algae.

3. A wall according to claim 1, wherein the micoorganisms are photosynthetic bacteria.

4. A process for the preparation of a transparent wall according to claim 1, wherein it comprises the following stages:
   (a) preparing a liquid mixture comprising polyurethane form precursor compositions and a suspension of microorganisms in a liquid nutrient medium,
   (b) introducing the mixture into a mould having two opposite walls, whereof only one had been impregnated with an agent able to open the pores of the foam,
   (c) forming the plastic material foam by reacting the precursor compositions present in the liquid mixture, and
   (d) removing the thus obtained wall from the mould.

5. A process according to claim 4, wherein the agent able to open the pore of the foam is a polyoxyalkylene with a high ethylene oxide content, a polyester polyol or an alkanol amine.

6. A process according to claim 5, wherein the polyoxyalkylene is polyethylene glycol.

7. A process according to claim 4, wherein the polyurethane form precursor compositions are a polyether polyol based on propylene oxide and ethylene oxide, as well as toluene diisocyanate.

8. A process according to claim 4, wherein the opposite walls of the mould are constituted by concentric tubes.

9. A process according to claim 4, wherein the opposite walls of the mould are flat plates.

10. A biophotoreactor for culturing microorganisms, wherein it comprises at least one transparent wall according to any one of the claims 1, to 3, wherein the face of said wall which is impermeable to the gases and liquids being exposed to a light source, and the opposite face of said wall having an open porosity is in contact with a liquid nutrient medium and with a gas for bringing about the growth of the microorganisms present in said wall and for permitting them to synthesize the desired products.

11. A biophotoreactor according to claim 10, wherein the transparent wall is shaped like a tube, whereof the outer surface constitutes a face which is impermeable to the gases and liquids, and wherein the nutrient medium and a gas are circulated within the said tube.

12. A biophotoreactor according to claim 10, wherein it compriese two superimposed transparent walls defining between them a gap for the circulation of the first liquid nutrient medium and a first gas and in this case the face which is impermeable to the gases and the liquids of the second transparent wall positioned beneath the first transparent wall is in contact with the first liquid nutrient medium circulating in the gap between the two walls, whilst the face having an open porosity of the second transparent wall is in contact with the second liquid nutrient medium and the second gas for ensuring the growth of the microorganisms is the second wall.

13. A biophotoreactor according to claim 12, wherein the first wall contains microalgae and the second wall contains photosynthetic bacteria.

14. A biophotoreactor according to claim 10, wherein it comprises two superimposed transparent walls defining between them a gap in which is circulated a liquid nutrient medium, the face having the open porosity of the first transparent wall and which is located above the second transparent wall in contact with the liquid nutrient medium and the face having the open porosity of the second transparent wall is also in contact with the liquid nutrient medium.

15. A biophotoreactor according to claim 14, wherein the first wall contains microalgae able to produce and release oxygen into the liquid nutrient medium and wherein the second wall contains microorganisms using oxygen for their growth.

* * * * *